(12) United States Patent
Wang et al.

(10) Patent No.: US 8,451,007 B2
(45) Date of Patent: May 28, 2013

(54) INPUT CIRCUIT FOR INDUCTIVE MEASUREMENTS OF THE CONDUCTIVITY OF A FLUID MEDIUM

(75) Inventors: Fengjin Wang, Shanghai (CN); Changlin Wang, Shanghai (CN)

(73) Assignee: Mettler-Toledo AG, Greifensee (CH)

( * ) Notice: Subject to any disclaimer, the term of this patent is extended or adjusted under 35 U.S.C. 154(b) by 322 days.

(21) Appl. No.: 13/006,089

(22) Filed: Jan. 13, 2011

(65) Prior Publication Data

US 2011/0140716 A1   Jun. 16, 2011

Related U.S. Application Data

(63) Continuation of application No. PCT/EP2009/005076, filed on Jul. 13, 2009.

(30) Foreign Application Priority Data

Jul. 14, 2008   (CN) .......................... 2008 1 0040546

(51) Int. Cl.
*G01N 27/60* (2006.01)
(52) U.S. Cl.
USPC .......................................... 324/445; 324/453

(58) Field of Classification Search
USPC .......................................... 324/439–446, 654
See application file for complete search history.

(56) References Cited

U.S. PATENT DOCUMENTS

| | | | |
|---|---|---|---|
| 2,542,057 A | | 2/1951 | Relis |
| 3,292,077 A | * | 12/1966 | Sloughter ..................... 324/445 |
| 4,220,920 A | | 9/1980 | Gross |
| 5,268,642 A | * | 12/1993 | Uchidomi ..................... 324/445 |
| 5,455,513 A | | 10/1995 | Brown et al. |
| 6,414,493 B1 | | 7/2002 | Rezvani |

* cited by examiner

*Primary Examiner* — Vincent Q Nguyen
(74) *Attorney, Agent, or Firm* — Standley Law Group LLP

(57) ABSTRACT

Exemplary embodiments of the invention include an input circuit for electromagnetic (inductive) measurements of the conductivity of liquids. The input circuit and the induction coil are directly coupled, and the arrangement includes a current-voltage converting circuit which accomplishes the transformation from current to voltage in the induction coil, and ensures the terminal voltage to be zero. Also there is an anti-saturation circuit which is composed of an integrating circuit and a voltage dividing circuit and serves to prevent saturation in the operational amplifier which is used for the current-voltage transformation. The circuit further includes features for the detection of an open-circuit failure of the sensor coil or cable.

20 Claims, 1 Drawing Sheet

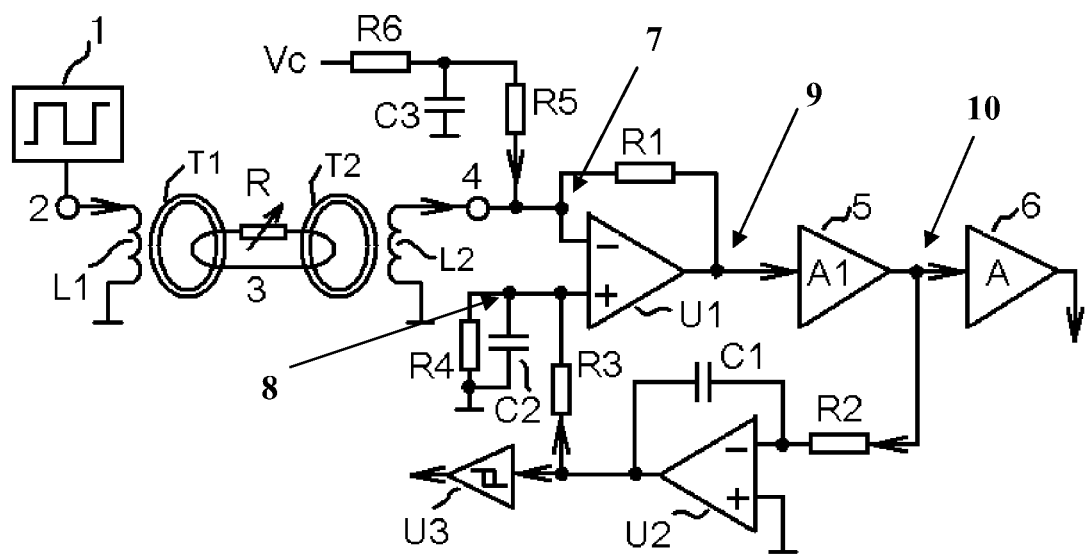

INPUT CIRCUIT FOR INDUCTIVE MEASUREMENTS OF THE CONDUCTIVITY OF A FLUID MEDIUM

CROSS-REFERENCE TO RELATED APPLICATIONS

This application is a continuation under 35 USC §120 of PCT/EP2009/005076, filed on 13 Jul. 2009 which is, in turn, entitled to, and claims, benefit of a right of priority under 35 USC §119 from Chinese Patent Application No. 200810040546.4, filed on 14 Jul. 2008. The content of each of these applications is incorporated by reference as if fully recited herein.

TECHNICAL FIELD

Exemplary embodiments of the present invention concern input circuits and corresponding measurement devices for inductive measurements of the electrical conductivity of a fluid medium, in particular a liquid or a solution.

BACKGROUND

The electrical conductivity of a liquid is an important analysis parameter of electrochemistry. Its measurement has a wide application in fields like the chemical industry, metallurgy, biology, medicine, grain testing, water conservancy, energy resources, and others. Conductivity measuring methods can be divided into two groups: contact-type and non-contact type.

A non-contact type measurement applies the principle of electromagnetic induction and is therefore also referred to as electromagnetic conductivity measuring method or inductive conductivity measuring method. As there is no contact between the conductive part of the measuring component and the measured liquid, sensors of this type possess the advantages of good solidity, corrosion resistance, non-polarization and long service life.

There has been a long history of development since the basic principle of electromagnetic measurement of the conductivity of a liquid was first invented and applied in practice. For example, the U.S. Pat. No. 2,542,057 to M. J. Relis opened the basic theory to the public in 1951. The sensor according to this reference employs a pair of coaxial magnetic rings, covered with corrosion-protective and electrically insulating material. The inner hole of the two magnetic rings allows the current path through the liquid. According to the electromagnetic induction principle, by supplying an alternating current to the excitation coil an alternating magnetic flux is generated in the magnetic ring carrying the excitation coil, which, in turn, generates an induction current through the loop in the measured liquid. The induction current generated in the loop represents the current loop which passes through both the excitation-side magnetic ring and the pickup-side magnetic ring. This current loop generates an AC magnetic flux in the magnetic ring, which generates in the induction coil an induced current, which in turn produces an induced electrical voltage at the induction coil. The induced current is related to the conductivity of the liquid. The induced current and the induced voltage of the induction coil (open-circuit voltage) is proportional to the current through the liquid. Thus, the conductivity of the liquid can be derived from the measurement of the induced current or the induced voltage. The conductivity G of the liquid can be calculated from the formula $G=C/R$, wherein C is the sensor cell constant and R is the equivalent resistance of the loop through the liquid.

In the past, the induced current or the induced voltage of the induction coil was measured by an electric bridge balance method. The bridge balance reduces the effect of stray magnetic or electric fields, which are related to an unwanted coupling between the coils. However this method has the disadvantages of low precision and a low level of automation. At present, due to the development of the modern electronic technologies, this method is rarely used.

To increase the sensitivity and the precision of the measurements and to reduce the magnetic properties of the coils, U.S. Pat. No. 5,455,513 A1 to Neil L. Brown, et al. proposes a system that uses a current-compensation method, also referred to as zero-current method. The induction current in the induction coil is balanced with the compensation current in the measuring device. This results in that the compensation current is subtracted from the induction current to produce a difference signal. This difference signal is processed by amplification, in-phase detection and integration to provide a direct current (DC), also known as continuous current or DC signal, which is proportional to the conductivity of the liquid.

For the generation of the compensation current a feedback circuit is introduced. Thereby the DC signal is processed by a switching multiplication and further amplifications to derive a phase shifted, square wave feedback signal, which is supplied via a feedback resistor to the induction coil. The circuit is configured to provide a negative feedback: in the case that the two currents in the above mentioned subtraction are not equal, the resulting difference signal causes the generation of a feedback action that will bring the circuit back to balance, which corresponds to a difference signal at zero value.

However, this method and the corresponding circuit is relatively complicated, because it has many complex and expensive components like a tuned filter amplifier, an in-phase detector, switching multiplier and numerous amplifiers. To change the measurement range, one normally has to change the parameters of all these components.

Another design of an input circuit is disclosed in U.S. Pat. No. 4,220,920 to Thomas A. O. Glass. In this case the induction coil is connected via a coupling capacitor to an operational amplifier, configured as a current-to-voltage converter. The capacitor separates the induction coil from the operational amplifier and serves to eliminate a DC offset. While this appears to be a simple solution, it also has some disadvantages: first, the alternating current could be attenuated to some extent by the DC-blocking capacitor; second, the size of this capacitor is large; and third, connecting the negative input of the operational amplifier and the induction coil via a DC-blocking capacitor can lead to oscillations. A circuit without DC-blocking capacitor is therefore preferable.

In the measurement of conductivity, it has also become more and more important to improve the reliability of the measuring process. If not investigated carefully, an open-circuit failure of the coils or cable wiring could easily be mistaken for a conductivity of zero (or a very low conductivity). U.S. Pat. No. 6,414,493 to Behzad Rezvani discloses a method wherein a single-turn coil is added to each of the two magnetic rings. A large resistor is arranged in series with each coil in order to get a certain bias. Under normal conditions, this bias can be corrected by calibration. But when open-circuit failure occurs at the coils or cables, the measuring circuit will exhibit a significant negative conductivity, which allows the open-circuit failure to be detected with the method. However, adding a coil to the ferrite rings makes the circuit more complicated.

SUMMARY OF THE INVENTION

An objective of the exemplary embodiments of the present invention is to overcome the drawbacks of the prior art, in particular exemplary embodiments provide a simpler and a cost effective circuit and a corresponding measuring device, which achieves accurate and reliable measurements of the conductivity of a fluid medium. A further objective is to provide an input circuit with a high adaptability to different measurement ranges. An additional objective of exemplary embodiments in accordance with the present invention is to provide an input circuit that is suitable to detect failures of the sensor, in particular the coils, the cable wiring and/or the input circuit.

The technical solution is provided by an input circuit, which comprises the features described in the independent claim. Further embodiments of the invention are disclosed in the additional dependent claims.

Exemplary embodiments of the present invention disclose an input circuit for the inductive measurement of the electrical conductivity of a fluid medium connectable via a measurement terminal to a sensor, which comprises an excitation coil for applying an excitation current to the fluid medium and an induction coil for receiving an inducted current, generated by the excitation current via the fluid medium, said input circuit comprising a control circuit, which is connected to the measurement terminal firstly with a first input to receive a signal corresponding to the inducted current and secondly via a first feedback loop with a first output to provide a first output signal, which serves to provide a compensation current, which at least partly compensates the induced current, and said control circuit comprising a second output to provide a second output signal, which corresponds to the electrical conductivity of the fluid medium. Thereby the control circuit comprises a second feedback loop, which connects the second output of the control circuit to a second input of the control circuit to provide a second input signal, which corresponds to the second output signal, and that the control circuit is configured to control the first output signal and/or the second output signal such that the second input signal is substantially equal to the first input signal. This way the exemplary embodiments according to the present invention have the advantage of a simple design, because both feedback loops can be designed with a few simple and stable components like a resistor or an integrator. Further the design provides high accuracy and high reliability and can easily be adapted to different measurement ranges.

The exemplary embodiments are based on amplitude measurements rather than phase shift measurements known form the prior art. Therefore the input circuit can be build with a simple design by avoiding complex components like an in-phase detector or a switching multiplier.

The high accuracy and high reliability is achieved by directly compensating a possibly arising DC offset with the compensation current. Therefore a coupling capacity with its disadvantages like attenuation, large size or oscillations can be avoided.

An exemplary input circuit according to the invention is especially advantageous at a low level of conductivity of the fluid medium. In these situations, the conductivity is generally not linear because the residual electromagnetic and electrostatic couplings are mutually affected by resistive leakage through the fluid medium and by the influence of eddy currents in flow of the fluid medium. Accordingly, these non-linear effects can effectively be compensated for, because feedback compensation is based on a continuous adjustment and not on a calibration at a single point, which is generally inadequate to effect a good compensation.

The compensation according to exemplary embodiments is achieved by an internal compensating apparatus, which is easy to operate, simple and cost-effective. Further the measurement of the conductivity of the fluid medium can be performed without the use of electrodes or of a supplementary compensating network.

In a first embodiment of the invention the first feedback loop comprises a first resistor, which is connected on one side to the first output of the control circuit and on the other side to the measurement terminal.

In another embodiment the control circuit comprises an operational amplifier, its negative input being the first input of the control circuit, its positive input being the second input of the control circuit and its output being the first output of the control circuit. This way the second feedback loop in the input circuit of the present invention works as an anti-saturation circuit, which serves to ensure that the DC component at the measurement terminal is zero in order to avoid saturation of the operational amplifier. This improves the accuracy and the reliability of the measurements.

In still another embodiment, the signal from the induction coil is a current and that the control circuit is configured to convert this signal to a corresponding voltage.

In additional embodiments, the signal of the first output is amplified to provide the signal of the second output with a first-stage operational amplifier, which in particular is configured such that its output voltage is proportional to the induced current of the induction coil.

In other embodiments, the second feedback loop is configured to provide the second input signal according to a direct current (DC) component of the output signal and/or the second feedback loop comprises an integration circuit, which is connected with its input to the second output of the control circuit and with its output, in particular via a third resistor, to the second input of the control circuit. Preferably the integration circuit comprises an operational amplifier, its negative input being connected firstly via a first capacitor to its output and secondly via a second resistor to the second output of the control circuit and its positive input being connected to ground.

Exemplary embodiments may also include an input circuit for electromagnetic (inductive) measurements of the conductivity of liquids which is distinguished by a simple design, high accuracy, and high reliability.

Other exemplary embodiments also include an input circuit for electromagnetic (inductive) measurements of the conductivity of liquids, wherein said conductivity is measured by immersing a sensor into a liquid. The sensor includes at least two ferrite rings, one of which carries an excitation coil and the other carries an induction coil. The input circuit contains a current-voltage converting circuit, which has one first input terminal, one output terminal and one feedback terminal, wherein the first input terminal is connected to the first terminal of the induction coil. The current which is induced in the induction coil is converted to a voltage and then outputted by the first output terminal of the current-voltage circuit. An integrating circuit which is connected to the current-voltage converting circuit generates a feedback voltage with the DC component of the output voltage. A voltage dividing circuit connects the integrating circuit to the feedback terminal of the current-voltage converting circuit. The voltage dividing circuit provides the appropriate voltage for the feedback terminal of the current-voltage converting circuit.

In still another embodiment of the above input circuit for electromagnetic (inductive) measurements of the conductivity of liquids, comprise a current-voltage conversion circuit, the current-voltage conversion circuit includes a first operational amplifier, which has a positive input terminal, a negative input terminal and an output terminal. The negative input terminal acts as the input terminal for the current-voltage converting circuit; the positive input terminal acts as the feedback terminal for the current-voltage converting circuit; and the output terminal acts as the output terminal for the current-voltage converting circuit. The negative input terminal is connected to the first terminal of the induction coil whose second terminal is connected to ground. The output terminal and the negative terminal of the first operational amplifier are connected through a first resistor.

Other embodiments of the above input circuit for electromagnetic (inductive) measurements of the conductivity of liquids include a filtering capacitor, which connects the feedback terminal to ground.

Still other embodiments of the above input circuit for electromagnetic (inductive) measurements of the conductivity of liquids further include a first-stage operational amplifier, which connects the current-voltage converting circuit and the integrating circuit.

In another embodiment of the above input circuit for electromagnetic (inductive) measurements of the conductivity of liquids, the output voltage of the first-stage operational amplifier is proportional to the induction current of the induction coil.

In a further embodiment of the input circuit, the integrating circuit includes a second operational amplifier which has a positive input terminal, a negative input terminal and an output terminal being the output of the integration circuit, wherein the positive input terminal is connected to ground. The integrating circuit also includes a second resistor which connects the second output of the control circuit to the negative input of the second operational amplifier, and an integrating capacitor, which connects the output and negative input terminals of the second operational amplifier.

In other embodiments of the input circuit for electromagnetic (inductive) measurements of the conductivity of liquids, the integrating circuit is configured such that its time constant of the integrating circuit is much larger than the period of the alternating excitation current.

In an additional embodiment of the input circuit, the input circuit includes a third resistor which connects the output of the integrating circuit to the second input of the control circuit, and a fourth resistor which connects the second input of the control circuit to ground. This forms a voltage divider which allows for an easy realization of the discrimination between the output level of the integration circuit a further detection circuit.

In another embodiment the input circuit also includes an open-circuit failure detecting circuit, which includes a fifth resistor connecting a power supply to the induction coil and serves to introduce a DC test current and a voltage level detector, which is connected to the integrating circuit, operable to indicate that the induction coil and a corresponding cable wiring are working normally when a voltage, which corresponds to the DC test current, at its input is lower than a threshold voltage, and to indicate an open-circuit failure in the induction coil or the cable wiring when the voltage at its input is higher than the threshold voltage.

In other embodiments the input circuit also includes a filtering circuit connected between the positive power supply and the fifth resistor. This filtering circuit contains a sixth resistor which connects the positive power supply and via a fifth resistor to the first input of the control circuit, and a filtering capacitor, one of whose terminals is connected to ground and the other is connected to the common node of the fifth resistor and sixth resistor.

The exemplary input circuit of the present invention includes an anti-saturation circuit made up of the aforementioned integrating circuit and voltage dividing circuit, which serves to ensure that the DC component of the circuit output is zero in order to avoid saturation of the operational amplifier and improve the accuracy and reliability of the measurement. In addition, one of the implementations of the present invention includes the functionality of detecting open-circuit failure. A very small DC current is introduced at the negative input terminal of the operational amplifier. If the induction coil and the cable wiring are working normally—as the DC resistance of the induction coil and cables is very small—the small DC current will flow to ground through the induction coil instead of through the I-V converting circuit. The output voltage of the anti-saturation circuit is very small. Conversely, if there is an open-circuit failure on the induction coil or its cable, the added small DC current will flow into the I-V converting circuit. In this case, the output voltage of the integrator of the anti-saturation circuit is very high. Therefore, by monitoring the output voltage of the integrator of the anti-saturation circuit it is possible to detect an open-circuit failure in the induction coil or the cable wiring.

Compared to the existing state-of-the-art measuring circuit, exemplary embodiments of the present invention introduce a method with the following advantages: it uses a simpler and lower-cost circuit to precisely measure the conductivity of the liquid. Without modifying the sensor, it uses a simple and low-cost circuit to detect an open-circuit failure of the induction coil and the connecting cable, which makes the measurement result very reliable.

In addition, the exemplary embodiments may include a measuring device with a current source and an input circuit disclosed above, the input circuit being operably connected to an appropriate sensor, wherein the excitation coil is connected to the current source for receiving the excitation current, and in particular that the second output of the control circuit is connected to a main operational amplifier to amplify the output signal.

In another embodiment, the measuring device comprises a inductive conductivity sensor, which is operably connected to the input circuit, wherein the sensor is immersed into the fluid medium, in particular into a liquid or a solution, and/or wherein the excitation coil and/or the induction coil of the sensor is carried by a toroidal core, in particular a ferrite ring or a magnetic ring.

Below is a further description of the advantages and characteristics of the present invention with references to the appended drawing FIG. 1, which represents the basic method of electromagnetically (inductively) measuring the conductivity and schematically illustrates the principle of one implementation of an exemplary input circuit according to the present invention.

In the electromagnetic measuring method for the conductivity of liquids disclosed by the present invention, the induction current of the induction coil is measured directly. An exemplary circuit according to the present invention uses a direct coupling method, omitting a big DC-blocking capacitor. It uses an operational amplifier with a feedback resistor to realize the basic I-V conversion. It also uses an anti-saturation circuit to avoid the saturation of the operational amplifier.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 1 is a simplified exemplary circuit for inductive measurements of the conductivity of liquids with a current generating circuit, a sensor and an embodiment of an input circuit according to the invention.

DETAILED DESCRIPTION OF EXEMPLARY EMBODIMENT(S)

FIG. 1 illustrates a strongly simplified exemplary circuit suitable for inductive measurements of the conductivity of liquids. The circuit comprises a current generating circuit, a sensor and an embodiment of an input circuit according to the invention as simplified electrical schema. In this embodiment, the control circuit comprises an I-V converting circuit, which converts the signal, which is received at the first input of the control circuit.

The circuit has a first input 7 to receive a signal corresponding to the inducted current a second input of the control circuit 8, a first output 9 to provide a first output signal and a second output 10 to provide a second output signal, which corresponds to the electrical conductivity of the fluid medium.

The sensor contains the excitation coil L1, a first ferrite ring T1, a second ferrite ring T2, and the induction coil L2. The loop through the measured liquid is identified as 3 and its equivalent resistance is R. The basic principle of electromagnetically measuring the conductivity of a liquid is to supply the excitation coil L1 of the sensor with an alternating voltage 1 of a certain amplitude, and to use a control circuit, which is embodied in the example as an I-V conversion circuit made up of R1 and U1 to transform the alternating induction current of the induction coil L2 into an alternating voltage. The virtual ground connection of the operational amplifier of the current-voltage converting circuit I-V ensures that the terminal voltage of the induction coil is zero, because it is a basic characteristic of an operational amplifier that the potentials of the positive and negative input are equal. The positive input is also known as non-inverting input, whereas the negative input is known as inverting input. Next, through both the first-stage operational amplifier 5 and the main operational amplifier 6 and after rectification, a DC voltage is obtained which is proportional to the conductivity of the measured liquid. After A/D conversion and appropriate arithmetic processing, the conductivity is obtained as a result.

R1 and U1 form the basic current-voltage converting circuit. The induction coil L2 and the output of U1 of the I-V converting circuit are directly connected. Assuming that the gain of the first-stage operational amplifier 5 is $A_1$ and the gain of the main operational amplifier 6 is A, the CPU will normally determine the appropriate gain in accordance with the measured liquid in order to deliver a signal with enough precision to the ND converter. In this case, the first-stage operational amplifier can be omitted, which means $A_1=1$. Otherwise, the output voltage $V_5$ of the first-stage operational amplifier is:

$$V_5 = I_{L2} \times R_1 \times A_1$$

Wherein $I_{L2}$ represents the current on L2. For direct coupling to the I-V converting circuit, the DC resistance of the induction coil and cables is very small, thus the output of the operational amplifier could easily be driven into saturation, which would prevent the circuit from working normally and reliably. Therefore, an anti-saturation circuit is needed which is made up of a second resistor R2, an integrating capacitor C1, a second operational amplifier U2, a third and a fourth resistor R3, R4, and a filtering capacitor C2. Among them, R2, C1, U2 form an integration circuit. Its time constant (R2×C1) is very large, i.e. much larger than the excitation period. The excitation frequency is for example 5 kHz. The integration circuit integrates the output voltage V5 of the first-stage operational amplifier 5. If a DC component is present in V5, for example a negative component, the output of the integration circuit U2 will increase. The output voltage of U2 is divided by R3, R4. The dividing node is connected to the positive input terminal of U1, which increases the DC component in the output of U1. This is a negative feedback. The process will continue until the DC component of V5 is zero. In summary, this is an anti-saturation circuit which is suitable for an AC amplifier to keep the DC component at zero. C2 serves to further reduce the noise of the input of U1 but can be omitted for a less demanding application and for cost savings. Note that the time constant made up of R3, C2 and R4 must be far smaller than R2×C1; otherwise the anti-saturation circuit would become self-oscillating. The voltage-dividing circuit made up of R4, R3 keeps R2×C1 limited, which means that the capacitor C1 could be of a rather small size and lower cost. Because the time constant R2×C1 is very large, the impact of the anti-saturation circuit on the alternating component with the frequency of the excitation voltage can be ignored.

Based on the above circuit, the functionality of detecting the open-circuit failure can be achieved through a simple design improvement, adding a circuit made up of a fifth resistor R5, a filtering capacitor C3, and a sixth resistor R6. A voltage level detector U3 is set to detect an open-circuit failure of the induction coil and the cable wiring. R6 and C3 form a low-pass filter, and R5 is a large resistor. If the induction coil and the cables have proper continuity, as the DC resistance of the coil is very small, the insignificant DC current will flow through the coil instead of the I-V converting circuit. Consequently, the DC output of the integration circuit U2 will be almost zero. However, when there is an open circuit in the induction coil L2 or the wiring cable, the DC current flowing through R5 will continue through R1, and accordingly the output of U1 will become negative. In this case, the anti-saturation circuit will take effect, which always keeps the DC component of the output of the operational amplifier 5 at the zero point. Consequently the DC component of the output of U1 is held at the zero point. Thus, the output of the integration circuit U2 is:

$$V_{U2} = Vc \times \frac{R1}{R1 + R5 + R6} \times \frac{R4 + R3}{R4}$$

For example, with assumed values of Vc=3.3V, R6=100 kΩ, R5=1MΩ, R1=20 kΩ, R4=2KΩ, R3=100 kΩ, $V_{u2}$=3.0V, a significant change of the output of U2 could easily be detected by a voltage level detector U3 connected to the output of the integration circuit U2. A low voltage at the input of U3 means that the coil and cable wiring work normally. Conversely, a high voltage indicates an open-circuit failure in the induction coil or the cable wiring. The voltage level detector U3 can have a threshold voltage in order to discriminate between high and low input voltage levels. The output of the level detector U3 can be used for example to trigger an alarm. The voltage level detector U3 can be a gate circuit. It is preferable to use a device like a Schmitt trigger consisting for example of two gates 74HC14 connected in series.

Another advantage of the voltage divider formed by R3 and R4 is that the discrimination between output levels of U2 by the level detector U3 can be more easily realized.

R6 and C3 form a low-pass filter to block excitation-frequency-related electric noise which can be introduced by the power source Vc and which could affect the I-V converting circuit and thus have a negative effect on the measurement. The low-pass filter of R6 and C3 should mend the situation. However, unless there is a strong necessity, this low-pass filter can be omitted. In case of an open-circuit failure in the induction coil or the cable wiring the input of the voltage level detector U3 is in this case close to:

$$V_{U2} = V_C \times \frac{R1}{R1 + R5} \times \frac{R4 + R3}{R4}$$

Because the added DC current is very small, for example 3 μA (3.3V/1.1M), which would never bring the coil into saturation, the accuracy of the measurement is not affected.

In an exemplary embodiment of the invention, besides the above mentioned parameters, other component values which can be selected are in particular: R2=2.2MΩ, C1=100 nF, C2=10 nF, C3=100 nF, A1=10, A=1 to 100.

The terms, symbols, expressions and examples used in the description above are not in any way meant to limit the scope of the invention, but serve only to illustrate certain aspects of the invention.

The embodiments described above only represent preferred embodiments of the present invention. Various equivalent substitutions and modifications can be made by one skilled in the art based on the foregoing description. Nevertheless, all these substitutions and modifications based on the embodiments of the present invention fall within the spirit of the present invention and the scope as defined in the following claims:

What is claimed is:

1. An input circuit for the inductive measurement of the electrical conductivity of a fluid medium connected by a measurement terminal to a sensor, the sensor includes an excitation coil for applying an excitation current to the fluid medium and an induction coil for receiving an inducted current generated by the excitation current via the fluid medium, said input circuit comprising:
a control circuit having a first input and a first output, the first input receiving a signal corresponding to the induced current from the measurement terminal connected thereto, the first output connected to a first feedback loop to provide a first output signal, the first output signal is a compensation current partially compensating for the induced current, the control circuit further comprising:
a second output providing a second output signal corresponding to the electrical conductivity of the fluid medium; and
a second feedback loop connecting the second output of the control circuit to a second input of the control circuit to provide a second input signal corresponding to the second output signal, wherein the control circuit is configured to control the first output signal and the second output signal such that the second and first input signals remain substantially equal.

2. The input circuit of claim 1, wherein the first feedback loop comprises a first resistor having a first side and a second side, the first side connected to the first output of the control circuit and the second side connected to the measurement terminal.

3. The input circuit of claim 1, wherein the control circuit further comprises an operational amplifier having a negative input, a positive input and an output, wherein the negative input is the first input of the control circuit, the positive input is the second input of the control circuit, and the output is the first output of the control circuit.

4. The input circuit of claim 1, wherein a signal from the induction coil is a current and the control circuit is configured to convert said current to a corresponding voltage.

5. The input circuit of claim 1, further comprising a first-stage operational amplifier amplifying the signal of the first output to provide the signal of the second output, wherein an output voltage of the first-stage operational amplifier is proportional to an induced current of the induction coil.

6. The input circuit of claim 1, wherein the second feedback loop comprises:
an integration circuit, said integration circuit having an input and an output, the input connected to the second output of the control circuit and the output connected to the second input of the circuit control via a third resistor.

7. The input circuit of claim 6, wherein the integrating circuit has a time constant larger than the period of the excitation current.

8. The input circuit of claim 1, further comprising:
a current-voltage converting circuit having a first input terminal, a first output terminal and a feedback terminal, the first input terminal connected to a first terminal of the induction coil, the current-voltage converting circuit converts the current induced in the induction coil to a voltage and outputs said voltage by the first output terminal, wherein the output voltage is proportional to the induced current;
an integrating circuit connected to the current-voltage converting circuit, the integrating circuit generating a feedback voltage with the DC component of the voltage output; and
a voltage dividing circuit connecting the integrating circuit and the feedback terminal of the current-voltage converting circuit, the voltage dividing circuit providing an appropriate voltage to feed the appropriate voltage to the feedback terminal of the current-voltage converting circuit.

9. The input circuit of claim 8, wherein the integrating circuit comprises:
a second operational amplifier having a positive input, a negative input and an output terminal, the output terminal being the output of an integrating circuit and the positive input is connected to ground;
a second resistor connecting the second output of the control circuit and the negative input of the second operational amplifier; and
an integrating capacitor connecting the output of the integrated circuit and the negative input of the second operational amplifier.

10. The input circuit of claim 9, further comprising:
a third resistor connecting the output of the integrating circuit and the second input of the control circuit; and
a fourth resistor interposed between the second input of the control circuit and ground.

11. The input circuit of claim 10, further comprising:
an open-circuit failure detecting circuit, including:
a fifth resistor interposed between a power supply and the induction coil so as to introduce a DC test current; and a voltage level detector is connected to the integration circuit, the voltage level detector indicates that the induction coil and a corresponding cable wring are working normally when a voltage, corresponding to the DC test current, at the input of the voltage level detector is lower than a threshold voltage and the voltage level detector indicates an open-circuit failure in the induction coil or the cable wring when the voltage at the input of the voltage level detector is higher than the threshold voltage.

12. The input circuit of claim 10, further comprising a filtering circuit interposed between the power supply and the fifth resistor, the filtering circuit includes:
a sixth resistor, the sixth resistor connects a positive power supply, via a fifth resistor, to the first input of the control circuit; and
a filtering capacitor having a first and second terminal, the first terminal connected to ground and the second terminal to a common node of the fifth and sixth resistors.

13. The input circuit of claim 1, wherein said conductivity of the fluid medium is measured by immersion of the sensor in the fluid medium, the sensor includes at least a first and second ferrite ring, the first ferrite ring carries an excitation coil and the second ferrite ring carries an induction coil.

14. The input circuit of claim 1, further comprising:
a filtering capacitor interposed between the second input of the control circuit and ground.

15. A measuring device, comprising:
a current source; and
an input circuit according to claim 1, the input circuit being connected to an appropriate sensor, wherein the excitation coil is connected to the current source so as to receive an excitation current and the second output of the control circuit is connected to a main operational amplifier.

16. The measuring device of claim 15, further comprising:
an inductive conductivity sensor connected to the input circuit, the inductive conductivity sensor immersed into the fluid wherein the excitation coil and the induction coil are carried by a toroidal core.

17. An input circuit for the inductive measurement of the electrical conductivity of a fluid medium connected by a measurement terminal to a sensor, the sensor includes an excitation coil for applying an excitation current to the fluid medium and an induction coil for receiving an inducted current generated by the excitation current via the fluid medium, said input circuit comprising:
a control circuit, said control circuit including:
a first input, the first input receiving a signal corresponding to the induced current from the measurement terminal connected thereto;
a first output connected to a first feedback loop to provide a first output signal, the first output signal is a compensation current partially compensating for the induced current, the first feedback loop having a first resistor interposed between the first output of the control circuit and the measurement terminal;
a second output providing a second output signal corresponding to the electrical conductivity of the fluid medium; and
a second feedback loop connecting the second out to a second input of the control circuit to provide a second input signal corresponding to the second output signal, wherein the control circuit is configured to control the first output signal and the second output signal such that the second and first input signals remain substantially equal.

18. The input circuit of claim 17, wherein the control circuit further comprises an operational amplifier having a negative input, a positive input and an output, wherein the negative input is the first input of the control circuit, the positive input is the second input of the control circuit, and the output is the first output of the control circuit.

19. The input circuit of claim 17, wherein a signal from the induction coil is a current and the control circuit is configured to convert said current to a corresponding voltage.

20. The input circuit of claim 17, further comprising a first-stage amplifier amplifying the signal of the first output to provide the signal of the second output, wherein an output voltage of the first-stage operational amplifier is proportional to an induced current of the induction coil.

* * * * *